United States Patent [19]

Bilweis

[11] Patent Number: 5,242,427
[45] Date of Patent: Sep. 7, 1993

[54] SURGICAL INSTRUMENT FORMING A TROCAR

[75] Inventor: Joseph Bilweis, Noisy LeRoi, France

[73] Assignee: Ethicon, Inc., Somerville, N.J.

[21] Appl. No.: 787,497

[22] Filed: Nov. 4, 1991

[30] Foreign Application Priority Data

Nov. 6, 1990 [FR] France .................. 90 13713

[51] Int. Cl.⁵ ............................. A61M 5/00
[52] U.S. Cl. ..................... 604/264; 604/164; 604/165; 606/185
[58] Field of Search ............... 604/134, 158, 164–165, 604/194, 264, 272, 157, 166, 110, 198, 263; 606/167, 184–185

[56] References Cited

U.S. PATENT DOCUMENTS

| | | |
|---|---|---|
| 3,539,034 | 11/1970 | Taffeen . |
| 3,595,230 | 7/1971 | Suyeoka et al. ............. 604/164 |
| 4,013,080 | 3/1977 | Froning ..................... 604/165 |
| 4,609,370 | 9/1986 | Morrison .................... 604/165 |
| 4,650,472 | 3/1987 | Bates ........................ 604/158 |
| 4,654,030 | 3/1987 | Moll et al. ................. 604/165 |
| 4,846,805 | 7/1989 | Sitar ......................... 604/165 |
| 4,952,207 | 8/1990 | Lemieux ..................... 604/164 |
| 4,973,316 | 11/1990 | Dysarz ....................... 604/195 |
| 4,994,042 | 2/1991 | Vadher ....................... 604/165 |
| 5,129,884 | 7/1992 | Dysorz ....................... 604/164 |

FOREIGN PATENT DOCUMENTS

| | | | |
|---|---|---|---|
| 265972 | 10/1913 | Fed. Rep. of Germany | 604/158 |
| 0135364 | 3/1985 | United Kingdom . | |
| 0350291 | 1/1990 | United Kingdom . | |

Primary Examiner—C. Fred Rosenbaum
Assistant Examiner—Corrine Maglione
Attorney, Agent, or Firm—Emil Richard Skula

[57] ABSTRACT

A surgical instrument of the trocar type, comprising a cannula, a needle engaged in the cannula, and manually controlled locking means suitable for selectively locking the needle in translation relative to the cannula.

4 Claims, 2 Drawing Sheets

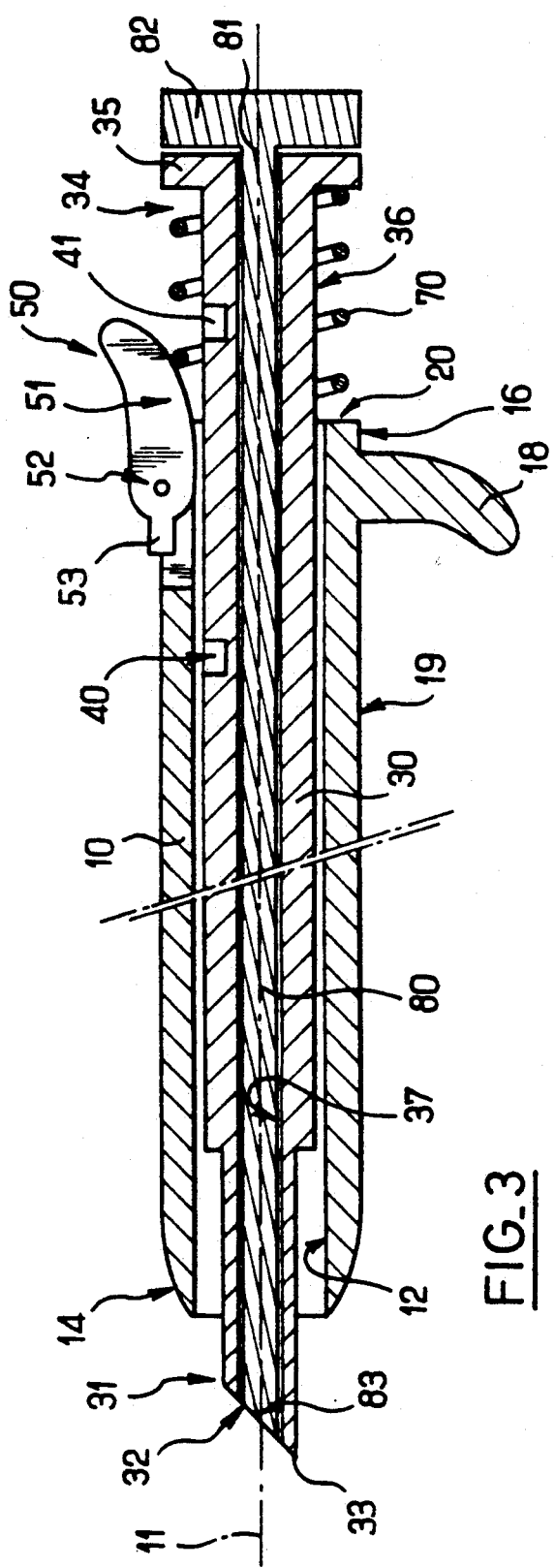
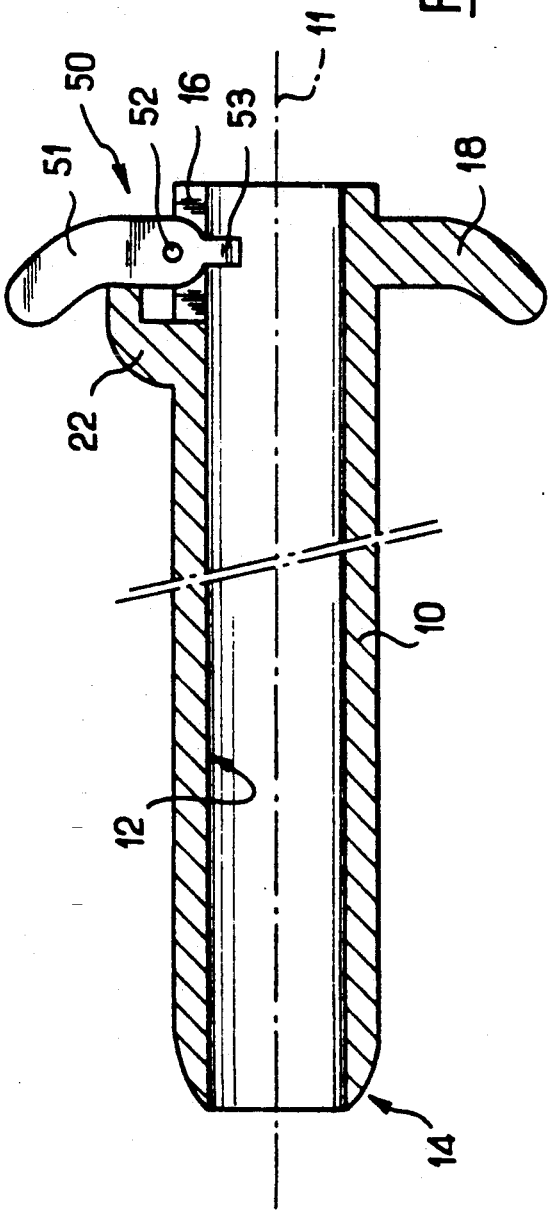
FIG. 3
FIG. 4

SURGICAL INSTRUMENT FORMING A TROCAR

BACKGROUND OF THE INVENTION

The present invention relates to the field of surgical instruments.

A main object of the present invention is to provide a novel surgical instrument of the trocar type suitable for performing punctures, in particular for withdrawing or injecting fluid, or for inserting a catheter.

SUMMARY OF THE INVENTION

According to the present invention, this main object is achieved by a surgical instrument comprising a cannula, a hollow, sharp-pointed needle engaged in the cannula, and manually controlled locking means suitable for selectively locking the needle in translation relative to the cannula.

According to another advantageous feature of the present invention, the manually controlled locking means are designed to define two locking positions between the needle and the cannula: a rest first position in which the sharp point of the needle is located inside the cannula, and a working second position in which the sharp point of the needle is located outside the cannula.

According to another advantageous feature of the present invention, the manually controlled locking means comprise a trigger pivoted on the cannula and designed to engage at least one catch formed on the outside surface of the needle.

According to another advantageous feature of the present invention, the needle is urged towards its rest position by a resilient member.

According to another advantageous feature of the present invention, a sliding rod is provided in the lumen of the hollow needle.

BRIEF DESCRIPTION OF THE DRAWINGS

Embodiments of the invention are described by way of example with reference to the accompanying drawings, in which:

FIG. 3 is a similar longitudinal axial section view through the same surgical instrument, but in an intermediate position between its above-mentioned rest position and working position; and FIG. 4 is a diagrammatic longitudinal axial section through a cannula from a variant embodiment of the present invention.

DETAILED DESCRIPTION

Figure 1:
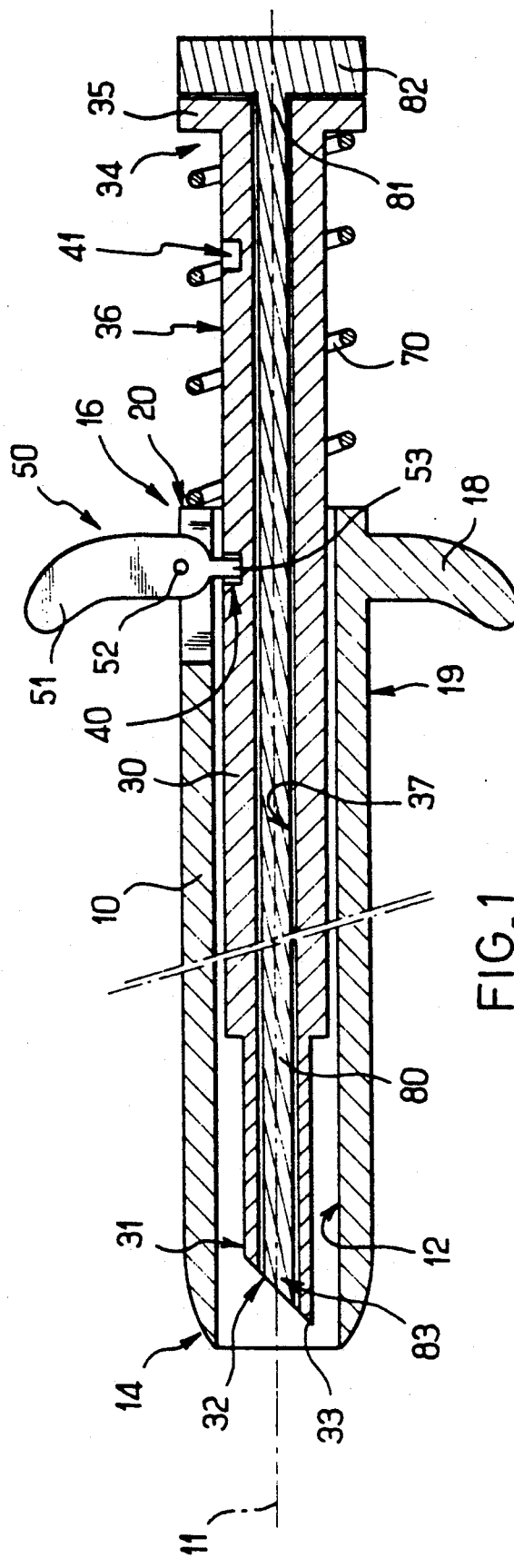
FIG. 1 is a diagrammatic longitudinal axial section view through a surgical instrument of the present invention in its rest position.
Figure 2:
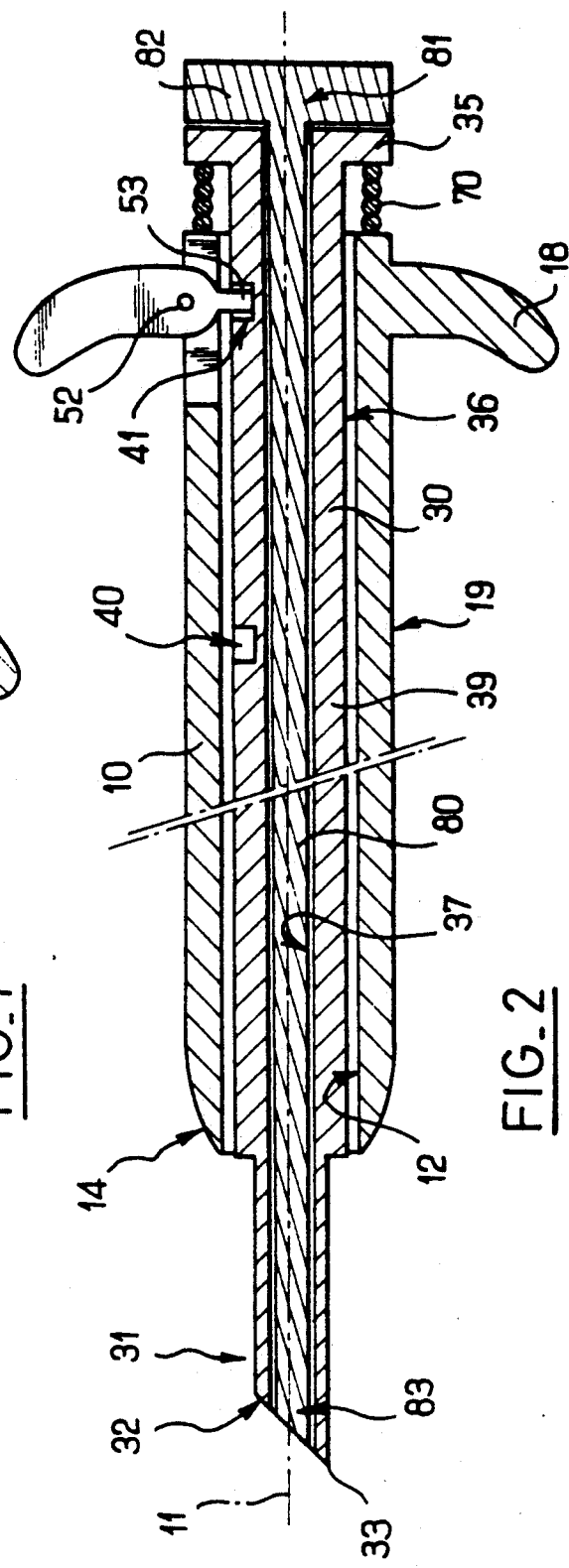
FIG. 2 is a similar longitudinal axial section through the same surgical instrument, but in its working position.

Accompanying FIGS. 1 to 3 show a surgical instrument comprising a cannula 10, a sharp-pointed needle 30, and manually controlled locking means 50.

The longitudinal internal lumen of the cannula 10 is referenced 12. This lumen is centered on the longitudinal axis 11 of the cannula.

The proximal end 14 of the cannula is rounded to avoid injuring tissue.

The distal end 16 of the cannula 10 is provided with handle means 18. There are numerous possible ways in which the handle means 18 may be embodied. For example, they may comprise at least one finger 18 projecting from the outside surface 19 of the cannula transversely to the axis 11, or a collar projecting from the outside surface 19 of the cannula 10 and centered on the axis 11.

As used herein, the convention concerning the terms "proximal" and "distal" relates to being near or far from the site at which surgery is being performed. The active part of the instrument is said to be at its "proximal" end, the part held by the surgeon is said to be at its "distal" end.

The locking means 50 suitable for preventing the needle 30 from moving in translation relative to the cannula 10 are provided at the distal end 16 of the cannula 10.

The needle 30 is engaged in the lumen 12 of the cannula 10. The proximal end 31 of the needle 30 is a tapering end. The proximal end 31 of the needle 30 is preferably delimited by a face 32 that slopes relative to the axis 11. The face 32 thus defines a sharp point 33 at the proximal end 31 of the needle.

The distal end 34 of the needle is provided with a disk 35 of larger diameter.

In the particular embodiment shown in FIGS. 1 to 3, and presently considered as being the preferred embodiment, the manually controlled locking means comprise a trigger 51 suitable for engaging in catches formed in the outside surface 36 of the needle.

More precisely, the trigger is pivoted on the cannula 10 about an axis 52 that extends transversely to the longitudinal axis 11 of the cannula.

The trigger 51 may be pivoted about the axis 52 by means of a stub axle engaged in a fork formed in the body of the cannula 10.

The body of the trigger 51 extends beyond the axis 52 towards the axis 11 in the form of a finger 53. The finger is designed to be engaged in one or other of two hollow catches referenced 40 and 41 and formed in the outside surface 36 of the needle 30.

The two catches 40 and 41 are axially spaced apart. More precisely, the positions of the two catches 40 and 41 are such that when the finger 53 of the trigger 51 is engaged in the catch 40 that is closer to the proximal end 31 of the needle 30, then the sharp point 33 of the needle is withdrawn inside the cannula 10. In contrast, when the finger 53 is placed in the second catch 41 closer to the distal end 34 of the needle 30, as shown in FIG. 2, then the sharp point 33 of the needle 30 projects considerably beyond the proximal end 14 of the cannula 10.

The needle 30 is preferably urged towards its rest position shown in FIG. 1 by a resilient member.

This resilient member is preferably constituted by a helical spring 70 engaged on the needle 30 between the disk 35 provided at the distal end of the needle and the face 20 extending transversely to the axis 11 and delimiting the distal end 16 of the cannula 10.

As shown in the accompanying figures, the needle 30 is hollow and has a longitudinal channel referenced 37 passing therealong. A rod or mandrel 80 may be engaged temporarily inside the channel 37 of the needle 30 to close the channel. To enable the needle 80 to be withdrawn, the distal end 81 thereof is provided with a knurled head 82, or with any equivalent means.

It is also preferable for the proximal end 83 of the needle to be chamfered so that the face 32 of the needle's sharp point is filled in without discontinuity.

As shown in FIG. 1, and as mentioned above, when the finger 53 of the trigger 51 is engaged in the catch 40 of the needle 30 closer to the proximal end thereof, the needle 30 is prevented from moving in translation relative to the cannula in a rest position such that the sharp point 33 of the needle 30 is withdrawn inside the cannula 10. In this rest position as shown in FIG. 1, the surgical instrument may be moved close to tissue, or inserted into a cavity such as the abdominal cavity, without any risk of injury or trauma for the surrounding tissues or organs.

To enable the needle 30 to be used, it suffices merely to pull the trigger 50 so that the finger 53 disengages the catch 40, as shown in FIG. 3. The needle 30 can then be displaced freely in translation relative to the cannula 10. If the surgeon so desires, the needle 30 can be locked in its position projecting from the cannula 10 by engaging the finger 53 in the second catch 41. The working position obtained in this way is shown in FIG. 2. In this position, the sharp point 33 of the needle projects well clear from the proximal end 14 of the cannula 10.

This working position may be used to perform injections via the channel 37 of the needle 30, or to withdraw fluid via the same channel 37, or else to insert a catheter via the channel 37.

When the trigger 51 is released, the spring 70 returns the needle 30 to its rest position as shown in FIG. 1. Once the needle has been withdrawn into the cannula 10, the instrument can be withdrawn without any risk of damaging surrounding tissues.

In the intermediate state shown in FIG. 3 between the rest position of FIG. 1 and the working position of FIG. 2, the needle 30 can be moved freely in translation backwards or forwards relative to the cannula 10. In this state, the needle 30 may be used, for example, to perform punctures.

Naturally, when the channel 37 of the needle 30 is used for performing injections, taking samples, or inserting a catheter, the needle 80 must be withdrawn.

Naturally, the present invention is not limited to the particular embodiment described above, but extends to any variant coming within the spirit of the invention.

In particular, the structure of the manually controlled locking means 50 may be subject to numerous variants.

Where applicable, the cannula 30 may be provided with means that prevent the trigger 51 from rotating anticlockwise from its radial position relative to the axis 11 as shown in FIGS. 1 and 2. In this case, the needle 30 cannot be returned from its working position to its rest position by the spring 70 when the trigger 51 is released by the user. It is then necessary to urge the needle 30 forwards a little in order to allow the finger 53 to be withdrawn by rotating the trigger 51 clockwise so as to allow the needle to be returned to its rest position by the spring 70. Such means preventing the trigger 51 from rotating anticlockwise from the radial position shown in FIGS. 1 and 2 may be constituted by abutments level with the fork carrying the pivoted trigger 51. Such means are shown diagrammatically in the form of an abutment 22 in FIG. 4.

The accompanying figures are naturally diagrammatic. In particular, the relative dimensions of the cannula 10, the needle 30, and the locking means 50 all of which are shown diagrammatically, are not limiting in any way.

In it also possible to envisage providing more than two catches 40, 41 in the needle 30, thereby defining more than two stable positions for the needle 30 relative to the cannula 10. Such a disposition makes it possible to accurately control the extent to which the needle 30 is extended relative to the cannula 10.

In addition, the trigger 51 may be associated with resilient means urging it towards its radial position relative to the axis 11, as shown in FIGS. 1 and 2, in which the locking finger 53 penetrates into a catch 40 or 41 of the needle. Such resilient means may be formed, for example, by a helical spring engaged about the pivot axis 52 and having its ends respectively engaging the cannula 10 and the trigger 51.

I claim:

1. A surgical instrument of the trocar type, comprising:

a cannula having a longitudinal internal lumen centered on a longitudinal axis, said cannula having a first end which is rounded to avoid injuring tissue and second end provided with handle means;

a hollow needle engaged in said lumen of the cannula, said needle having a longitudinal channel, a first sharp-pointed end adjacent to said first end of the cannula and a second end which is adjacent to said second end of the cannula and outside the second end of the cannula, the second end of the needle having an abutment of larger diameter than the diameter of the cannula lumen, said hollow needle having furthermore an outside longitudinal surface provided with two longitudinally spaced recessed catches;

manually controlled locking means comprising a trigger pivoted on the cannula about an axis that extends transversely to the longitudinal axis of the cannula to selectively engage said recessed catches provided in the outside surface of the hollow needle in order to selectively lock the needle in translation relative to the cannula in two locking positions: a first rest position in which the first-sharp-pointed end of the needle is located inside the cannula and a second working position in which the first sharp-pointed end of the needle is located outside of the cannula; and, a resilient helical spring engaged between the second end of the cannula and the abutment provided at the second end of said hollow needle, so as to urge the needle towards its rest position relative to the cannula.

2. The instrument of claim 1 further comprising a removable rod slidably engaged in the channel of said hollow needle, said rod having a first end adjacent said second end of the hollow needle, which is provided with a knurled head, and a second end which is chamfered so as to flush up without discontinuity the first sharp-pointed end of the hollow needle when the knurled head of the removable rod rests on said second end of the hollow needle, so as to close selectively said channel of the needle.

3. The surgical instrument according to claim 1 wherein the cannula comprises means that limit rotation of said trigger.

4. The surgical instrument according to claim 1 further comprising resilient means urging the trigger in a radical position relative to the longitudinal axis of the cannula.

* * * * *